(12) United States Patent
Johe

(10) Patent No.: US 10,413,534 B2
(45) Date of Patent: Sep. 17, 2019

(54) AMELIORATION OF CERTAIN DEFICIENCIES DUE TO STROKE

(71) Applicant: NEURALSTEM, INC., Germantown, MD (US)

(72) Inventor: Karl K. Johe, Hallandale Beach, FL (US)

(73) Assignee: NEURALSTEM, INC., Germantown, MD (US)

( * ) Notice: Subject to any disclaimer, the term of this patent is extended or adjusted under 35 U.S.C. 154(b) by 0 days.

(21) Appl. No.: 15/895,881

(22) Filed: Feb. 13, 2018

(65) Prior Publication Data

US 2018/0228787 A1 Aug. 16, 2018

Related U.S. Application Data

(60) Provisional application No. 62/458,493, filed on Feb. 13, 2017, provisional application No. 62/582,856, filed on Nov. 7, 2017.

(51) Int. Cl.
*A61K 31/444* (2006.01)
*A61K 31/496* (2006.01)
*A61P 25/28* (2006.01)
*A61K 9/00* (2006.01)

(52) U.S. Cl.
CPC .......... *A61K 31/444* (2013.01); *A61K 9/0095* (2013.01); *A61K 31/496* (2013.01); *A61P 25/28* (2018.01)

(58) Field of Classification Search
CPC .................... A61K 31/444; A61K 31/496
See application file for complete search history.

(56) References Cited

U.S. PATENT DOCUMENTS

| 8,362,262 | B2 | 1/2013 | Kelleher-Andersson et al. |
| 9,572,807 | B2 | 2/2017 | Johe |
| 2002/0035094 | A1* | 3/2002 | Mantlo ................ C07D 213/73 514/131 |
| 2007/0275987 | A1 | 11/2007 | Conte et al. |
| 2015/0359792 | A1* | 12/2015 | Johe ..................... A61K 31/496 514/253.13 |
| 2016/0090358 | A1* | 3/2016 | Venkatraman ....... C07D 213/74 544/365 |

FOREIGN PATENT DOCUMENTS

WO   WO-2015/195567   12/2015

OTHER PUBLICATIONS

Tajiri et al. J. Cell. Physiol., 2017, vol. 232, pp. 2731-2740 (Year: 2017).*
International Search Report for PCT/US2018/018014, dated Jun. 11, 2018, 4 pages.
Kokaia et al., "Neural stem cell-based therapy for ischemic stroke," Trans Stroke Res (2011) 2(3):272-278.
Pubchem, Substance Record for SID 147588916, Available Date: Oct. 22, 2012. Retrieved Feb. 24, 2019. Retrieved from https://pubchem.ncbi.nlm.nih.gov/substance/147588916/version/1#section=Top.
Pubchem, Substance Record for SID 164321482, Available Date: Nov. 1, 2013. Retrieved Feb. 24, 2019. Retrieved from https://pubchem.ncbi.nlm.nih.gov/substance/164321482#section=2D-Structure.
Sun et al., "Fluoxetine Enhances Neurogenesis in Aged Rats with Cortical Infarcts, but This is not Reflected in a Behavioral Recovery," J Mol Neurosci (2016) 58(2):233-242.

* cited by examiner

*Primary Examiner* — James D. Anderson
(74) *Attorney, Agent, or Firm* — Morrison & Foerster LLP

(57) ABSTRACT

Motor skill deficits and cognitive deficits associated with stroke and secondary neuronal cell death are ameliorated by treatment with pharmaceutically acceptable salts of 2-amino substituted nicotinamides.

9 Claims, 2 Drawing Sheets

AMELIORATION OF CERTAIN DEFICIENCIES DUE TO STROKE

CROSS-REFERENCE TO RELATED APPLICATIONS

This application claims priority from U.S. provisional application 62/458,493 filed 13 Feb. 2017 and U.S. provisional application 62/582,856 filed 7 Nov. 2017, the disclosures of which are herein incorporated by reference in their entirety.

TECHNICAL FIELD

The invention relates to treatment of stroke victims with compounds that ameliorate the loss of motor skills and of cognitive function loss associated with stroke. More particularly, it concerns the use of salts of 2-amino substituted nicotinamides for this purpose.

BACKGROUND ART

Among the many undesirable sequelae of ischemic stroke is the failure to recover motor skills. Current treatments for stroke are generally inadequate to prevent loss of motor skills which are resistant to recovery. Although it has been hypothesized that motor skills, among other deficits resulting from stroke, may be benefited from neurogenesis, leading, for example, to attempts to treat subjects using stem cells as sources of neuronal expansion (for example, Kokaia, Z., et al., *Transl. Stroke Res.* (2011) 2:272-278). Agents that enhanced neurogenesis in aged rats with cortical infarcts, however, did not effect behavioral recovery (Sun, X., et al., *J. Mol. Neurosci.* (2016) 58:233-242). Other negative effects include deficiencies in cognitive function.

A family of U.S. granted patents, represented by, for example, U.S. Pat. No. 8,362,262, discloses low molecular weight compounds that are capable of stimulating neuronal growth. These documents suggest that the compounds, which are shown to enhance neuronal growth, may be useful in the treatment of stroke; however, there is no disclosure that sustained subsequent treatment of stroke victims would be useful in the recovery of motor skills, of cognitive skills or enhancement of regeneration of neurons destroyed as secondary effects of stroke. Subsequently, it was found that certain 2-amino-substituted nicotinamides disclosed in these patents were useful in treating depression, in particular, major depressive disorder in humans as described in PCT publication WO2015/195567 and corresponding U.S. Pat. No. 9,572,807. Oral administration is disclosed. However, the motor skills deficits and cognitive deficits associated with stroke are not addressed by these documents.

DISCLOSURE OF THE INVENTION

It has now been found that certain 2-amino-substituted nicotinamides and their salts are useful in recovery of motor skills and of cognitive function that are sequelae of stroke and in enhancing regeneration of certain neurons.

Accordingly, in one aspect, the invention is directed to a method to ameliorate the motor skill deficits and/or cognitive deficits associated with stroke by administering to a subject in need of such amelioration, a pharmaceutical composition wherein the active ingredient is a pharmaceutically acceptable salt of a 2-amino-substituted nicotinamide. In particular, the 2-amino-substituted nicotinamide is of the formula:

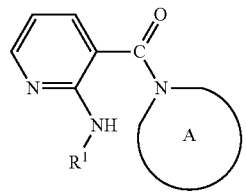

wherein $R^1$ is an alkyl of 3-8C and A is a 5- or 6-membered saturated ring optionally including an additional nitrogen which is unsubstituted or substituted with an additional nitrogen-containing substituent or A is a ring-opened form thereof.

Particular exemplified compounds include those of formula (2)

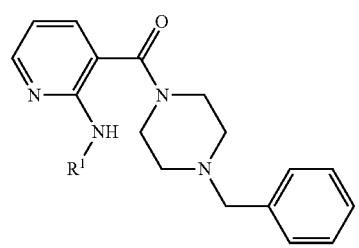

or formula (3)

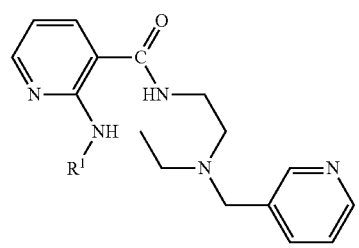

wherein $R^1$ is a branched alkyl group of 3-5C or of formula (4)

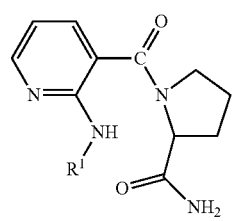

wherein $R^1$ is an alkyl group comprising a 5- or 6-membered ring.

In particular one embodiment of the compound of formula (2) or formula (3), $R^1$ is isoamyl. In formula (4) $R^1$ may be cyclohexyl —$CH_2$—NH—.

These same compounds also stimulate regrowth of neurons damaged as secondary to the initial stroke damage in the subject is that wherein $R^1$ is isoamyl.

The compounds useful in the invention are administered as their pharmaceutically acceptable salts and in particular phosphate salts. In some embodiments, the invention method further includes assessing the motor skills and/or cognitive function of the subject as a companion to the therapeutic treatment with the compositions of the invention.

MODES OF CARRYING OUT THE INVENTION

Figure 1:
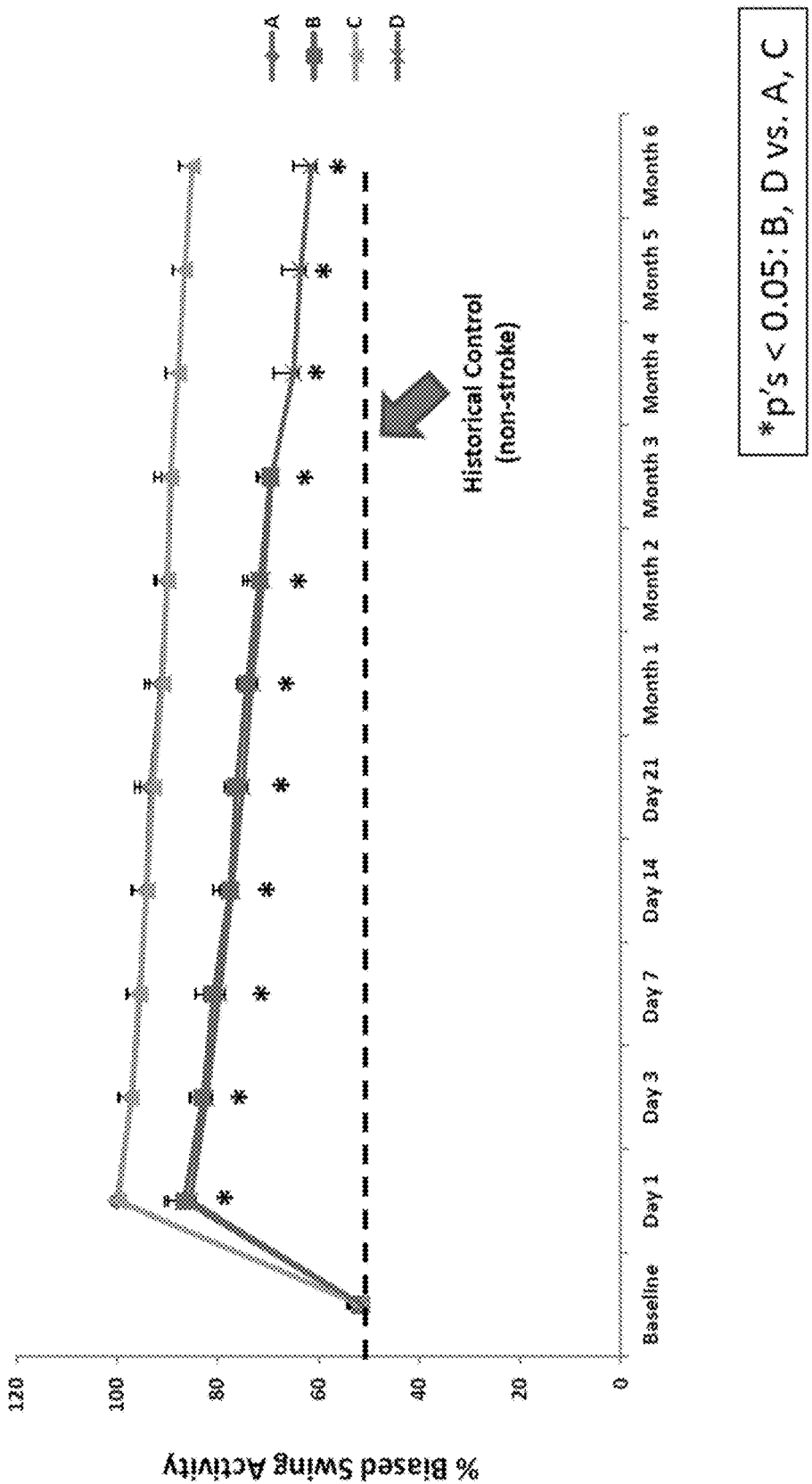
FIG. 1 shows the results of treated and untreated subjects subjected to the elevated body swing test. Results C and D represent treated subjects while A and B represent untreated subjects.

One difficult aspect of recovery from ischemic stroke is regaining motor skills such as balance, steadiness, muscular control and ability to manipulate appendages. The invention method is helpful in providing recovery of these essential skills. In addition, the methods of the invention restore the growth of neuronal cells in the brain that undergo secondary damage as opposed to those primarily affected by the ischemia as well as in the recovery of cognitive function.

The active agents useful in the methods of the invention have the general formula (1) noted above wherein $R^1$ is an alkyl of 3-8C and A is a 5- or 6-membered saturated ring optionally including an additional nitrogen or A is a ring-opened form thereof. Thus, $R^1$ may be, in formula (1), a straight or branched chain alkyl group of at least 3C, such as isopropyl, secondary butyl, n-butyl, isoamyl, sec-amyl, hexyl, isohexyl and the like or comprise a saturated ring. Preferably in formula (2) or (3), $R^1$ is a branched alkyl of 3-5C and, in formula (4), $R^1$ comprises a 5- or 6-membered saturated ring. Preferred embodiments of ring A are a piperidine or piperazine ring or ring opened forms thereof or a pyrrolidine ring. Typically, ring A is substituted with at least an additional nitrogen-containing substituent, including a substituent including an additional pyridine ring such as pyridyl methyl, or pyridyl ethyl or is a simpler substituent such as a carboxamide. Preferred forms of ring A are shown in formulas (2), (3) and (4) above along with appropriate substituents.

The compounds of the invention are administered in the form of their pharmaceutically acceptable salts such as halides, maleates, succinates, nitrates and the like. Particularly favored are phosphate salts.

The compounds of the invention are formulated in standard pharmaceutical formulations such as those found in *Remington's Pharmaceutical Sciences*, latest edition, Mack Publishing Co., Easton, Pa. and include formulations for oral administration and parenteral administration. Typically, the compounds are administered orally in the form of tablets, capsules or in formulations that are administered as syrups or any other standard formulation. In some instances, the formulations may be designed for delayed release or may be designed for more instantaneous delivery. A variety of formulations that would be suitable for the compounds of the invention is known in the art and is subject to the decision of the practitioner with regard to route of administration.

Dosage levels also depend on the judgment of the practitioner, but are generally in the range of 0.01 mg/kg to 1-2 g/kg.

In general, the subjects of the treatment will be humans, although it is useful to employ laboratory animals as well in order to assess appropriate dosages, routes of administration and formulations. Thus, the subjects of the invention include not only humans, but laboratory research animals such as rabbits, rats, mice and the like. In some instances, other mammalian subjects may be appropriate such as in veterinary contexts where the subject may be ovine, bovine or equine or the subject may be a companion animal such as dog or cat.

The frequency of administration and dosage schedules is also dependent on the practitioner and the dose may be chronic and on a daily basis, weekly basis or more frequent, or a single dosage may suffice. Typically treatment is continued daily over 6-12 weeks. The compounds of the invention may also be administered in combination with other active agents either in the same composition or sequentially.

The recovery of these functions can be measured by a number of evaluation tools. For cognitive function, these include evaluation of, for example, novel place recognition, novel object recognition, object and place recognition and recognition of temporal order. The analyses may also include fear conditioning.

A particularly useful diagnostic is measurement by Cog-Screen, a computer-administered cognitive test battery required by the U.S. Federal Aviation Administration (FAA) for evaluation of the neurocognitive functioning of pilots and which has also played a key role in the FDA drug approval and labeling process (CogScreen LLC, St Petersburg, Fla.). This includes analysis of Shifting Attention Test-Arrow Color Accuracy a measure of executive functioning; Shifting Attention Test-Arrow Direction Reaction Time Correct, a measure of attention; Symbol Digit Coding-Delayed Recall Accuracy, a measure of memory and Shifting Attention Test-Instruction Number Incorrect, which is a measure of working memory. One or a combination of these aspects or a subset thereof may be employed.

For motor skills, these include the elevated body swing tests (EBST) and the Bederson neurological exam.

The following examples illustrate, but do not limit the invention.

Example 1

Recovery of Motor Skills

A. Stroke surgery. Sixty (60) adult Sprague-Dawley, male rats (weighing around 250 g at beginning of the study) received experimental stroke surgery using the middle cerebral artery occlusion (MCAo) model, under aseptic conditions. Mice were anesthetized with 1-2% isoflurane in nitrous oxide/oxygen (69%/30%) using a face mask and checked for pain reflexes. Under deep anesthesia, animals underwent the MCAo surgery which entails insertion of a filament through the carotid artery to reach the junction of the MCA, thus blocking the blood flow from the common carotid artery, as well as from the circle of Willis.

The right common carotid artery was identified and isolated through a ventral midline cervical incision and suture size 4-0, made of sterile, non-absorbable suture (Ethicon, Inc.), with the diameter of the suture tip tapered to 24 to 26-gauge size using a rubber cement. About 15 to 17 mm of the filament was inserted from the junction of the external and internal carotid arteries to block the MCA. The right MCA was occluded for one hour. A heating pad and a rectal thermometer allowed maintenance of body temperature within normal limits (37±0.3° C.).

To determine successful occlusion and reperfusion, a laser Doppler probe was placed at the distal end of the MCA and revealed at least 80% reduction in regional cerebral blood flow. To further ensure similar degree of stroke insults, physiological parameters including $P_aO_2$, $P_aCO_2$, and plasma pH measurements were monitored. Based on laser Doppler readouts and behavioral tests after MCAs, a total of 48 animals were enrolled in this study.

B. Drug Treatment. In the treated subjects, 30 mg/kg of the phosphate of formula (2) wherein $R^1$ is isoamyl (NSI-189 $H_3PO_4$ (mol. wt. 464.50)), 99.8% pure based on the weight of the API (active pharmaceutical ingredient) base without the weight of phosphate salt was administered orally in 0.03N HCl in deionized water (n=24) or vehicle (n=24) was administered following MCAo 6 hours after stroke, and daily for the next 12 weeks.

C. Motor and neurological tests. The elevated body swing test (EBST) and neurological exams were administered. EBST is conducted by holding the mouse by its tail and recording the direction of swings in a clear Plexiglas® box (40×40×35.5 cm). Each rat was gently picked up at the base of the tail, and elevated until the nose was at a height of 2 inches (5 cm) above the surface. The direction of the swing, either left or right, was counted once the animals head moves sideways approximately 10 degrees from the midline position of the body. After a single swing, the animal was placed back in the Plexiglas® box and allowed to move freely for 30 seconds prior to retesting. These steps were repeated 20 times for each animal.

About one hour after the EBST, the Bederson neurological exam was conducted using 3 tests: (1) forelimb retraction—measuring the ability of the rat to replace the forelimb after it was displaced laterally by 2 to 3 cm, graded from 0 (immediate replacement) to 3 (replacement after several seconds or no replacement); (2) beam walking ability, graded 0 for a rat that readily traversed a 2.4-cm-wide, 80-cm-long beam to 3 for a rat unable to stay on the beam for 10 seconds; and (3) bilateral forepaw grasp—the ability to hold onto a 2-mm-diameter steel rod, graded 0 for a rat with normal forepaw grasping behavior to 3 for a rat unable to grasp with the forepaws. The scores from all 3 tests, which were done over a period of about 15 minutes on each assessment day, were added to give a mean neurologic deficit score (maximum possible score, 9 points divided by 3 tests=3).

Rats were subjected to tests for EBST and neurological tests at baseline (prior to stroke), then at 1, 3, 7 days after stroke and at weekly intervals post-treatment.

Figure 2:
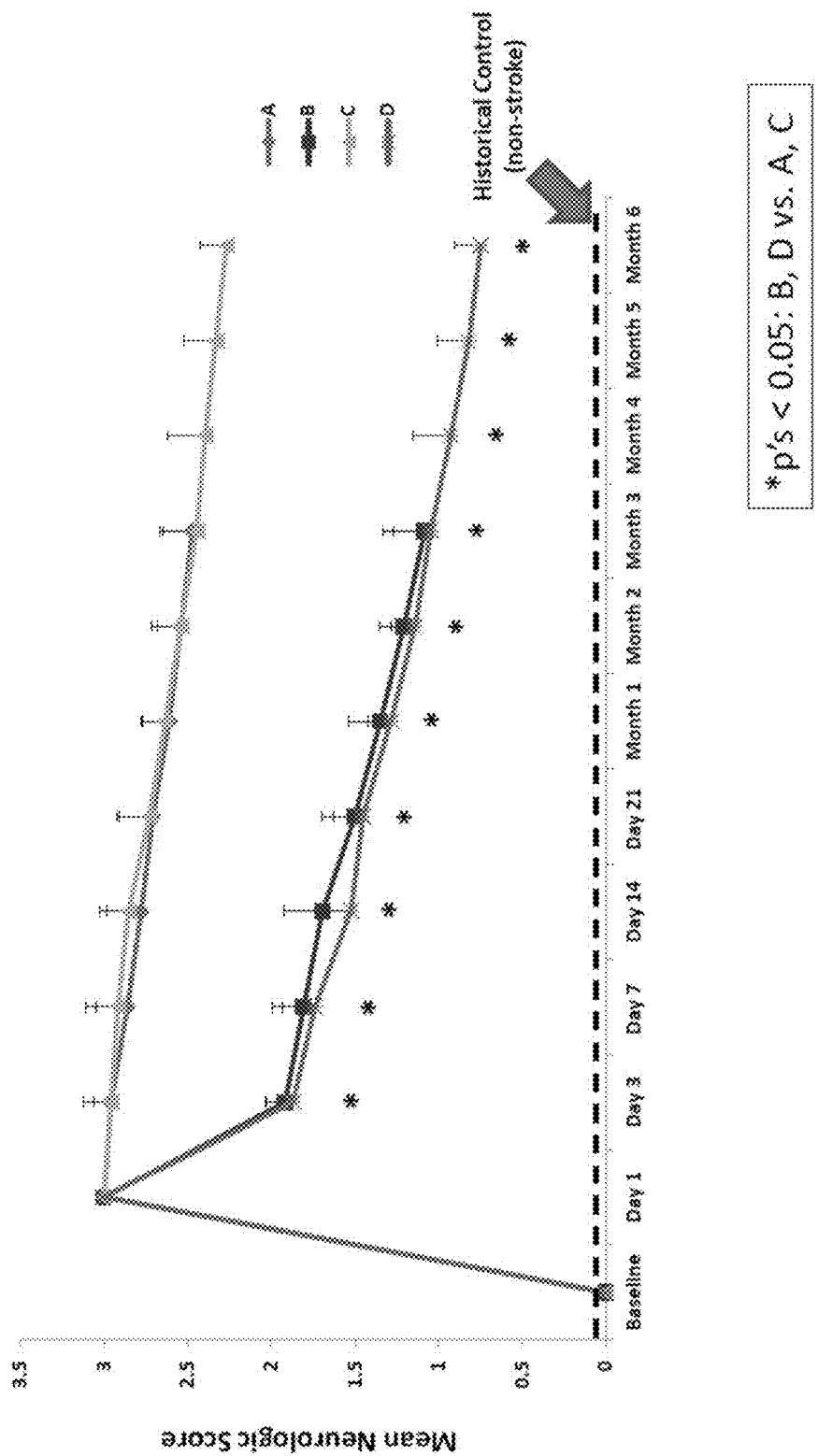
FIG. 2 shows the results of treated and untreated subjects with respect to a Bederson neurologic test involving three separate measurements of neurological aptitude. Again, lines B and D represent treated subjects and A and C represent untreated subjects.

As shown in FIGS. 1 and 2, treatment orally with the phosphate of formula (2) wherein $R^1$ is isoamyl (NSI-189 phosphate) was successful in restoring motor skills both in the EBST and in the Bederson neurological exam. As shown in FIG. 1, treated subjects (lines B and D) recovered performance in the EBST almost to baseline levels, whereas the controls showed no such recovery.

Similarly, in FIG. 2, the treated subjects, lines B and D, again showed performance approaching that of control even after 6 months. Treated rats showed control of motor skills as early as day 3 post stroke as compared to animals that received only vehicle (p<0.05) and the treated rats continued to improve over time compared to untreated animals not only during 12 weeks of drug treatment but even during the next 12 weeks after withdrawal of treatment (p<0.05).

Example 2

Enhancement of Repair of Neurons that have Undergone Secondary Cell Death

At scheduled intervals post-stroke (either 12 weeks or 24 weeks), rats of Example 1 were randomly euthanized (n=12 per treatment), perfused by transcardial perfusion with 4% paraformaldehyde. The brains were dissected, post-fixed for overnight in 4% paraformaldehyde, then subsequently immersed in 30% sucrose until immunohistochemical processing. Brain section preparations were designed to identify stroke-induced cerebral infarction and NSI-189-induced neurogenic effects.

Brains were embedded in gelatin blocks and sectioned on a freezing sliding microtome at 40-µm. The sections were washed in PBS 5×10 min to remove the antigen preservative solution. Endogenous peroxidase was blocked using 3% $H_2O_2$ for 15 minutes. The sections were then incubated in 1% Triton-X100 for 30 minutes, and then blocked with 5% Normal Horse Serum (NETS) for 1 hour. The sections were incubated with the primary antibody that binds Ki67 (1:2000, Cat. #: ab16667, Abcam, CA) or that binds MAP2 (1:2000, Cat. #: AB5622, Millipore, MA) overnight, rinsed 5×5 min in PBS prior to pre-incubation in 5% NHS for 1 hour, then incubated with the secondary antibody which corresponded to the respective host of the primary antibody (Donkey or Rabbit, 1:2000, Cat. #: 711-066-152, Jackson ImmunoResearch Laboratories, Inc, PA) for 90 minutes. After rinsing in PBS (5×5 min), the sections were incubated with peroxidase-conjugated streptavidin (1:5000, Cat. #: 016-030-084, Jackson ImmunoResearch Laboratories, Inc, PA) with 1% NHS. The sections were washed 5×5 min in PBS after the streptavidin, prior to developing with DAB (3,3'-Diaminobenzidine Tetrahydrochloride Hydrate, Cat #: 1001306853, Sigma-Aldrich, St. Louis, Mo.) and Nickel chloride. After DAB processing, the sections were rinsed, mounted, and air-dried overnight. The slides were dehydrated, and coverslipped with DPX Mounting Medium (Cat #: 13512, Electron Microscopy Sciences, Hatfield, Pa.).

The slides were imaged and reviewed under Nikon brightfield microscope (Nikon, Tokyo, Japan). The regions of interest (ROIs), including the cerebral cortex, the hippocampal subfields (CA1+CA2, CA3 and DG) were contoured rostro-caudally and the immunoreactivity of the MAP2 density was measured by Nikon NIS-Element software and Ki67+ cells counted rostro-caudally along the subgranular zone (SGZ) by Image-Pro Premier (v10.10), respectively. The slides were coded and blinded to the analysts during the course of the study. After completion, quantitative data were extracted and transferred for the statistical analysis (Prism, GraphPad®, La Jolla, Calif.). The data values between groups were compared using ANOVA with Tukey's post-hoc tests (p<0.05).

The results from stroke brains from both NSI-189 and vehicle-treated stroke rats at either 12 weeks and 24 weeks post-stroke showed that cerebral infarction as revealed by neuronal marker MAP2 expression in the cortex and striatum did not significantly differ between groups indicating absence of NSI-189 effects in reducing the primary stroke insult on the brain (p's>0.05), and the neurogenic niche subventricular zone (SVZ), which lies in proximity to the primary stroke insulted striatal region, and the remote hippocampal area, specifically the neurogenic subgranular zone (SGZ), exhibited comparable levels of Ki67 between NSI-189 and vehicle-treated stroke animals (p's>0.05). In contrast, examination of secondary cell death in the peri-infarct cortex revealed apparent upregulation of cell proliferation and neurogenesis as evidenced by increased Ki67 and MAP2 staining, respectively, in NSI-189-treated stroke animals compared to vehicle-treated stroke animals. NSI-189-treated stroke animals displayed significant increments in MAP2 density compared to vehicle-treated stroke animals, which were more pronounced in the hippocampus than the cortex, in that the amplified MAP2 density in the cerebral cortex was only detected at the 12-week period, whereas increased MAP2 density was found in the hippocampus for both 12-week and 24-week time points (p's<0.05). These data show an active remodeling of the stroke brain, characterized by cell proliferation and neuronal maturation preferentially in the cortex and hippocampal areas, respectively, undergoing secondary cell death as opposed to the striatal areas proximal to the primary stroke insulted region.

The invention claimed is:

1. A method to reduce deficits in motor skills and/or cognitive skills or to enhance endogenous repair of neurons that have undergone secondary cell death in a subject due to stroke, which method comprises administering to a subject in need of such reduction or enhancement an effective amount of a pharmaceutically acceptable salt NSI-189 of the formula:

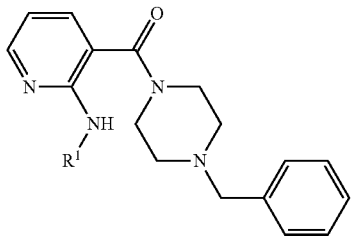

(2)

wherein $R^1$ is isoamyl.

2. The method of claim 1 wherein the salt is a phosphate salt.

3. The method of claim 2 wherein said administering is oral.

4. The method of claim 1 wherein said administering is over a period of at least 6 weeks subsequent to the stroke.

5. The method of claim 4 wherein said administering is over a period of at least 12 weeks subsequent to the stroke.

6. The method of claim 1 wherein said administering is initiated within 6 hours after said stroke.

7. The method of claim 1 which further includes subsequent testing of said subject for enhancement of recovery of said deficits.

8. The method of claim 7 wherein the deficit is of motor skills and the testing comprises the elevated body swing test (EBST) and/or the Bederson neurological exam.

9. The method of claim 6 wherein the deficit is of cognitive function and the testing comprises assessing executive function and/or attention and/or memory, and/or working memory, and/or assessing novel place recognition (NPR) and/or novel object recognition (NOR) and/or object in place (OiP) and/or temporal order (TO).

* * * * *